United States Patent [19]

Anselmo et al.

[11] 4,170,987

[45] Oct. 16, 1979

[54] MEDICAL DIAGNOSIS SYSTEM AND METHOD WITH MULTISPECTRAL IMAGING

[75] Inventors: Victor J. Anselmo, La Canada; Terrence H. Reilly, La Crescenta, both of Calif.

[73] Assignee: California Institute of Technology, Pasadena, Calif.

[21] Appl. No.: 855,364

[22] Filed: Nov. 28, 1977

[51] Int. Cl.$^2$ .............................................. A61B 6/00
[52] U.S. Cl. ................................... 128/665; 356/407; 356/406; 356/416
[58] Field of Search ........... 128/2 A, 2 L, 2 R, 2.1 R; 250/226; 356/51, 209, 212, 222, 229

[56] References Cited

U.S. PATENT DOCUMENTS

| | | | |
|---|---|---|---|
| 2,760,485 | 8/1956 | Adelman | 128/2 A |
| 3,405,268 | 10/1968 | Brunton | 356/51 |
| 3,531,208 | 9/1970 | Ward | 250/226 |
| 3,638,640 | 2/1972 | Shaw | 128/2 L |
| 3,765,776 | 10/1973 | Bravenec | 356/209 |
| 4,041,932 | 8/1977 | Fostick | 128/2 L |
| 4,114,604 | 9/1978 | Shaw et al. | 128/2 L |

Primary Examiner—William E. Kamm
Attorney, Agent, or Firm—Freilich, Hornbaker, Wasserman, Rosen & Fernandez

[57] ABSTRACT

A skin diagnosis system includes a scanning and optical arrangement whereby light reflected from each incremental area (pixel) of the skin is directed simultaneously to three separate light filters, e.g., IR, red, and green. As a result the three devices simultaneously produce three signals which are directly related to the reflectance of light of different wavelengths from the corresponding pixel. These three signals for each pixel after processing are used as inputs to one or more output devices to produce a visual color display and/or a hard copy color print, for one useable as a diagnostic aid by a physician.

15 Claims, 6 Drawing Figures

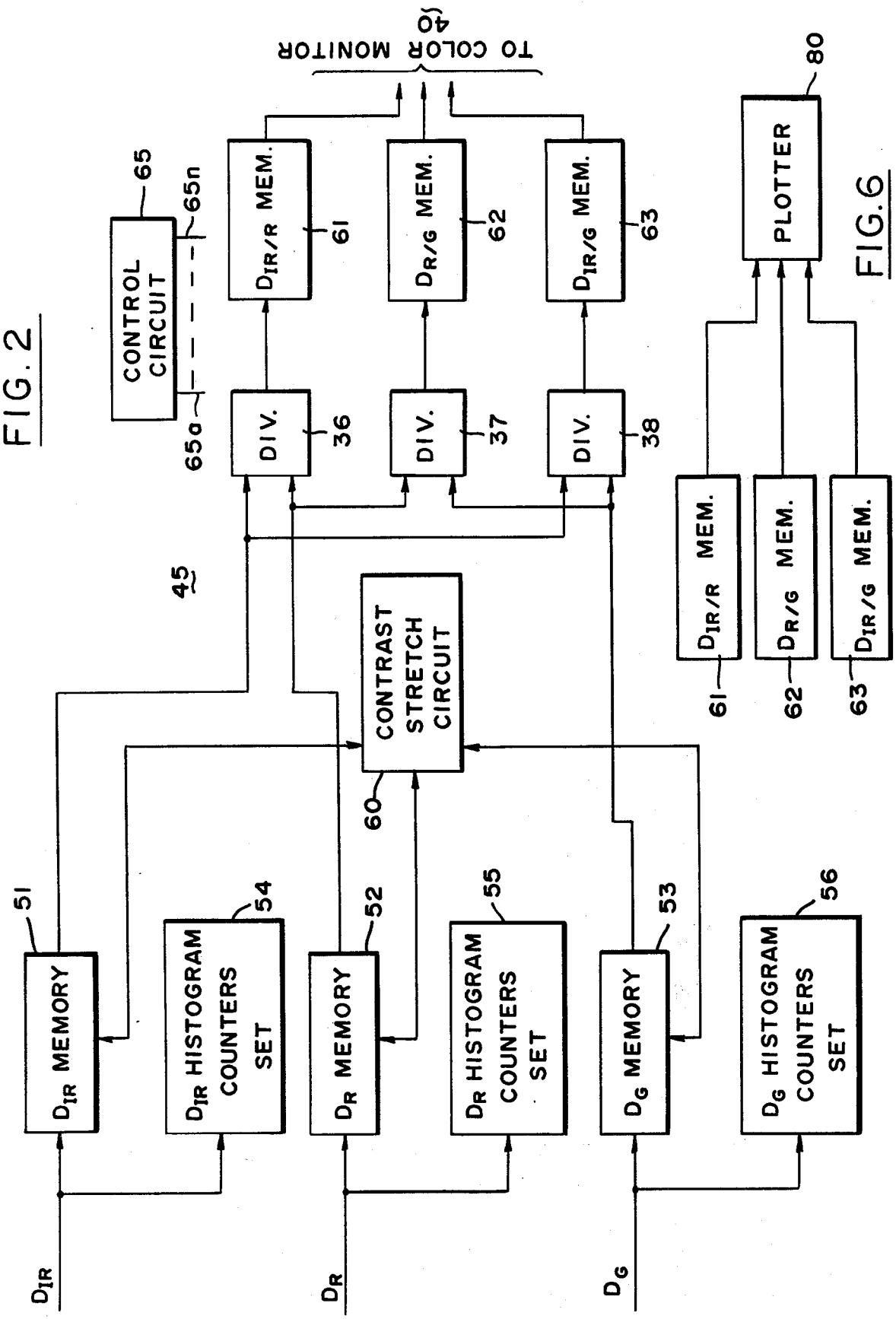

MEDICAL DIAGNOSIS SYSTEM AND METHOD WITH MULTISPECTRAL IMAGING

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The present invention generally relates to a medical diagnosis system and, more particularly, to a skin diagnosis system and method employing multispectral imaging.

2. Description of the Prior Art

The use of infrared photography as a potential tool for diagnosing tissue has been known for many years. More recently the use of photography to diagnose degrees of skin conditions, e.g., degrees of burns, has been proposed. The proposed diagnosis of burns is based on the use of visible and near-infrared photography. This proposed diagnosis is based on the fact that: (a) various wavelengths of light penetrate different depths into the skin; and (b) various types of tissue exhibit different degrees of light absorption at different wavelengths.

The recently proposed diagnosis of burns is based on the production of red, green, and infrared spectrally-filtered photographic images of the burned skin of a patient for determining areas of full-thickness burn as well as for differentiating between areas of full and partial-thickness burns. In accordance with the proposed burn diagnosis system three pictures are taken simultaneously through infrared, green, and red filters with three adjacently-located cameras of the area of interest.

After proper photographic processing three different photographs (transparencies) are produced. The first one represents the difference of the optical densities of the pictures, taken with the infrared and red filters. The second transparency represents the difference of the optical densities between the photographs, taken with the infrared and green filters, and the third transparency is one representing the difference of the optical densities of the pictures, taken with the red and green filters.

From these studies it has been found that one can determine the depth of the burn, i.e., whether it is a full-thickness or partial-thickness burn by observing the relative values of these differences of optical densities over a post-burn period. Also these three negatives are used to produce a color picture, which is also used in the diagnosis of the depth of the burn.

It is of great importance to diagnose the depth of the burn as early as possible in order to determine how the patient should be treated. Early primary excision of the full-thickness burn reduces the risk of infection, fibrosis, and loss of function. It also appears to provide the best surgical results in the shortest time. In many cases, however, it is very difficult to differentiate clinically between full and partial-thickness burns. In these cases the diagnosis depends heavily on the intuition and experience of the physician. Although the physician is aided by many tests covering sensory, mechanical, and thermal phenomena, the only positive method available to him is to wait three to four weeks until the natural healing pattern is established and the areas of irreversible damage are indicated. During the first weeks after the injury the wound is characterized by three zones: the zone of hyperaemia, the zone of stasis, and the zone of coagulation.

The zone of hyperaemia represents the most superficial wound. This zone appears red and continues to exhibit adequate circulation and metabolism necessary for viability. By the seventh day the wound is dry and healed with complete regeneration of the epidermis, but no apparent damage to the dermis.

The zone of stasis appears very much like the zone of hyperaemia, but upon testing, one finds the absence of metabolic processes. At the end of 24 hours, circulation ceases and complete stasis occurs. Between the third and seventh days, the zone of stasis turns brownish-white because the superficial surface of the dermis is avascular and necrotic, and the red cells which have previously colored the zone have been hemolyzed.

The zone of coagulation appears brownish-white and is characterized by complete obliteration of the lumina of the vessels and the subpapillary plexus, in the coagulation of the tissue.

It is desirable to excise the full-thickness burn early, during the first week if possible. Although it is known that the tissue of the zones of coagulation and stasis will be lost, it is not possible by inspection to determine whether these zones will include the full thickness of the skin or not. If excision is performed before a precise diagnosis of the full-thickness burn is made, the patient may suffer because sufficient tissue was not removed. Residual necrotic tissue will then remain as a source of sepsis requiring additional debridement, accompanied by additional pain and expense. If an excess of tissue is removed initially, the patient may suffer because he has lost viable tissue necessary for the healing process. Any delay or inaccuracy in the diagnosis of the full-thickness wound therefore increases the danger of sepsis. Sepsis is the single most common cause of death for the burned patient.

The prior proposed method of diagnosing burns of producing actual photographs on film which are then processed, as herebefore described, is capable of serving as a diagnostic aid. However, it has several very significant disadvantages. Ignoring cost, its primary disadvantage is the relatively long time period which has to elapse from the time the original pictures are taken until the final color pictures are produced. It is estimated that the time period would be about four to six weeks, which in most instances would be longer than absolutely required for proper treatment. This relatively long time period is due to several factors.

First, the optical density produced on any photographic film is related to various factors including the logarithm of the reflectance of light from an object to the film. Thus, to produce the ratio of the reflectance of light of different wavelengths from a subject which is directed to different cameras, the optical densities of the exposed films in these cameras has to be subtracted. Since in the proposed method three photographs are taken with three different cameras, even though they are located very close to one another, the resulting photographs have to be registered in a nonlinear fashion to insure the corresponding incremental areas (pixels) in pairs of these photographs overlay one another to produce correct optical ratio outputs. Also, picture enhancement is often required to increase the range of contrast. This is achievable by varying the $\gamma$ of the film. Only then can the ratios of the reflectance to corresponding pixels of different pairs of films be achieved, by subtracting the optical densities of the corresponding pixels on these films. Only thereafter can three transparencies be produced to finally produce the final composite color photograph which is used for the actual diagnosis.

It is estimated that even if one had full access to a relatively large and specialized data processing system, it would take at least a week to properly process the original three filtered photographs and produce the final color photograph for the burn diagnosis. Clearly, such lengthy processing, requiring highly experienced personnel would also be very costly. Thus even though the prior proposed burn diagnosis by means of taking different filtered photographs of the area of interest is feasible, it is not practical, nor is it capable of providing the diagnostic information early enough to help in the proper burn treatment. A need therefore exists for a new system and method for diagnosing skin conditions. It should be appreciated that a person's skin is but one type of surface tissue. Thus, generically a need exists for a new method and system for deriving information related to surface tissue conditions.

OBJECTS AND SUMMARY OF THE INVENTION

It is a primary object of the present invention to provide a new system and method for the diagnosis of skin or other surface tissue conditions.

Another object of the invention is to provide a new system and method for deriving skin condition information or information related to other surface tissue on a real or near-real time basis.

A further object of the invention is to provide a reliable method and system for obtaining information, helpful in the diagnosis of skin burns within a very short time, which is adequate for the proper treatment of the burns.

These and other objects of the invention are achieved in one embodiment of the invention by scanning the surface of a patient's skin, including the burned area and simultaneously generating for each incremental surface area (pixel) three signals, e.g., three numbers which are directly related to the reflectance of light of different wavelengths, e.g., IR, red and green from the pixel. After these three numbers for each pixel are generated they may be used to provide for the pixel three numerical ratios of different pairs of these numbers. The numerical ratios can be thought of as ratio numbers. The corresponding ratio numbers of each pixel are supplied in parallel as inputs to a color type monitor, e.g., a color television with corresponding ratio numbers of successively scanned pixels being supplied in sequence to produce a visual color display and/or to produce a hard copy, i.e., a permanent color photograph for use by the burn-diagnosing physician.

The novel features of the invention are set forth with particularity in the appended claims. The invention will best be understood from the following description when read in conjunction with the accompanying drawings.

BRIEF DESCRIPTION OF THE DRAWINGS

FIG. 2 is a block diagram of a simplified embodiment of a processor shown in FIG. 1;

FIG. 6 is a simple diagram of an arrangement for producing plots, like those shown in FIGS. 4 and 5.

DESCRIPTION OF THE PREFERRED EMBODIMENTS

Figure 1:
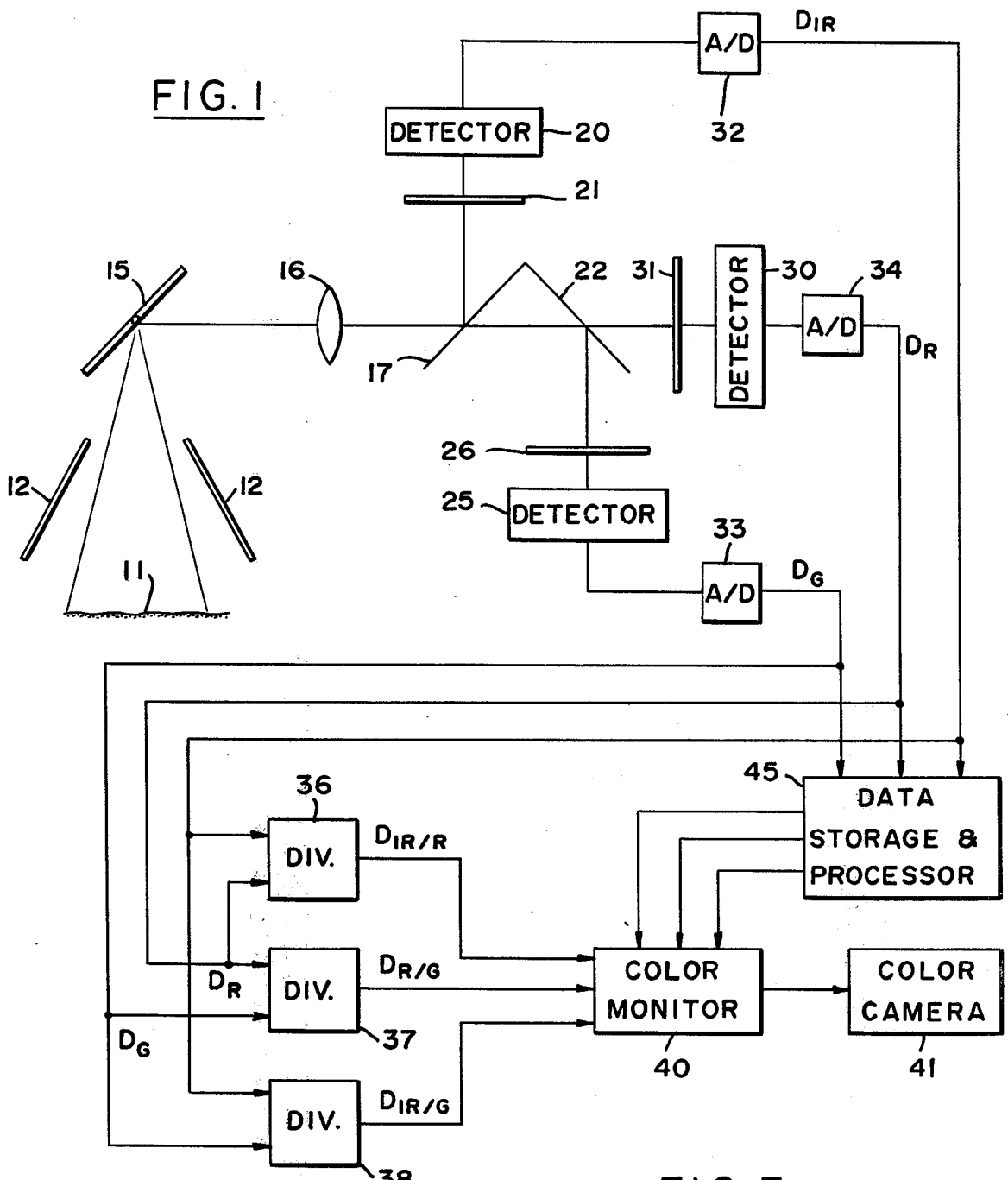
FIG. 1 is a general diagram useful in explaining the basic features of one embodiment of the present invention.

Attention is now directed to FIG. 1 in connection with which the novel features of the present invention will be described in the context of the diagnosis of burned skin of a patient. The patient's skin, designated by numeral 11, is illuminated by lamps 12. Light, reflected from the skin, is directed to a scanning or oscillating mirror 15, which directs the reflected light through appropriate optics, e.g., a lens 16 and a beam splitter 17 to a photosensitive detector 20 through a filter 21. The detector 20 may be a linear silicon diode array of the type well-known in the art. By means of the mirror 15 light from different incremental areas (pixels) of the skin 11 may be directed to different diodes of the detector 20. As is known, each silicon diode produces an analog signal which is directly related to the light which is directed thereto. Thus, as the mirror 15 scans one strip of the skin surface analog signals are provided by the detector 20 for successive pixels along that strip. By controlling the scan angle of mirror 15, successive strips of the skin 11 may be scanned and the light directed to the single linear detector 20 to produce a succession of analog signals. Each signal is directly related to the light reflected by a different pixel of the patient's skin. By the proper selection of filter 21 the analog signal from detector 20 is directly related only to reflected light of a particular wavelength or wavelength band, which reaches detector 20.

For explanatory purposes it is assumed that filter 21 is an infrared (IR) filter. Thus, the analog signal from detector 20 is directly related to the IR light, reflected by a particular pixel of the skin. The complete stream of analog signals from detector 20 is related to the IR, reflected by all the pixels of the skin which are scanned by the mirror 15.

Part of the light from mirror 15 passes through beam splitter 17 to another beam splitter 22, which reflects light to another detector 25 through a filter 26, and transmits light to yet another detector 30 through a filter 31. Detectors 25 and 30 are similar to detector 20, i.e., each is assumed to be a linear silicon diode array. For explanatory purposes, filters 26 and 31 are assumed to be green and red filters, respectively. Thus the analog signals from detectors 25 and 30 are respectively related to green and red light reflected by the skin pixels. By choosing the beam splitter 17 to have ⅓ reflectance and ⅔ transmissivity and that of beam splitter 22, ½ reflectance and ½ transmissivity equal amounts of light are directed to the three detectors.

It should be stressed that the light which is directed to the three detectors 20, 25 and 30 is simultaneously directed to them from a single skin pixel. Thus, as each pixel is scanned the three detectors 20, 25 and 30 simultaneously produce three analog signals which are directly related to the IR, green, and red light reflected by the particular pixel. Although heretofore the detectors 20, 25 and 30 were described as linear silicon diode arrays, it should be appreciated that other devices capable of providing signals directly related to light directed to them may be used.

The three analog signals which are produced by detectors 20, 25 and 30 simultaneously, for each skin pixel as it is scanned, are converted into digital numbers by analog-to-digital (A/D) converters 32, 33 and 34. The output of A/D converter 32 is a digital signal or number which is directly related to the IR reflected by a pixel, and is designated by $D_{IR}$. Likewise, the outputs of A/D converters 33 and 34 are digital numbers, directly related to the green and red light reflected by the same pixel and are designated by $D_G$ and $D_R$, respectively.

As shown in FIG. 1 for explanatory purposes, the digital numbers $D_{IR}$, $D_R$ and $D_G$ are supplied directly to three digital dividers 36, 37 and 38. Divider 36 is assumed to divide $D_{IR}$ by $D_R$ and produces a digital number $D_{IR/R}$ which effectively represents the ratio of the reflectance of IR by red light by a pixel. Likewise, divider 37 produces a digital number $D_{R/G}$ which is the ratio of the reflectance by the pixel of red and green light, while divider 38 produces a digital number $D_{IR/G}$ which is the ratio of the reflectance of IR and green light by the pixel.

These three ratio numbers, i.e., $D_{IR/R}$, $D_{R/G}$ and $D_{IR/G}$ may be fed directly to a color monitor 40, which will produce a visual color display of the scanned skin on effectively a real-time basis. The monitor 40, in addition to producing a visual color display, may be used to activate a color camera 41 to produce a hard color print. Thus, by scanning the skin 11 at different times during the critical period of interest a series of hard color prints can be produced. These prints can be used by the diagnosing physician to detect color changes, from which the different depths of burns can be determined, for use in the patient's treatment.

As will be pointed out hereafter, the system and method described so far, which effectively operates on a real-time basis i.e., produces color prints at the time the skin is scanned, may be modified by storing the outputs of the A/D converters 32–34, i.e., by first storing $D_{IR}$, $D_R$, and $D_G$, which are produced simultaneously for each skin pixel. Such stored numbers may then be operated upon to enhance the contrasts each set of numbers represents, and only then divide the enhanced numbers to produce the three ratio numbers for driving the color monitor. It is appreciated that such operation on numbers requires some finite time period. Since with modern equipment, data processing can be accomplished quite fast, the final color prints can be produced on a near-real-time basis. In FIG. 1 the data storage and processor to which $D_{IR}$, $D_R$ and $D_G$ are supplied and which may be used first to process these numbers, then produces the required ratio numbers and then drives the color monitor 40, is designated by 45, and for purposes of simplicity will be referred to as processor 45.

It should be appreciated that different circuit arrangements may be used in implementing processor 45. However, to complete the description one example of a simplified embodiment will be described, it being appreciated that the invention is not limited thereto. As shown in FIG. 2, the processor 45 includes a memory 51 to which the numbers $D_{IR}$ from A/D converter 32 are supplied successively for storage therein. Memory 51 may be thought of as the $D_{IR}$ memory, since its function is to store the $D_{IR}$ numbers. Assuming that the number of pixels is 1000, although in practice it is generally considerably larger, e.g., 16,000 pixels, and that the number of grey levels is 64, any $D_{IR}$ number may have a value from 0 to 63. For 1000 pixels memory 51 consists of 1000 6-bit bytes with each $D_{IR}$ stored in a different 6-bit byte. For explanatory purposes it is assumed that no exposure (or black) is represented by a $D_{IR}$ of 0 value and saturated exposure (white) is represented by a $D_{IR}$ of 63.

As each $D_{IR}$ is provided by converter 32, in addition to being stored in memory 51 it is also used to clock one of 64 counters (0-63) in a set of $D_{IR}$ histogram counters, designated in FIG. 2 by block 54. Basically if $D_{IR}=0$ the first counter in set 54 is clocked, if $D_{IR}=1$ the second counter is clocked, etc. Thus, at the end of scanning the 1000 pixels various ones of the counters in set 54 have been incremented. The total count in the 64 counters is 1000. By observing which counters were incremented more than others one can determine the degree of exposure of the skin and its reflectance of IR. For example, if in set 54 counters 60-63 have a total count of 800 out of 1000, it is obvious that the skin reflected an excessive amount of IR. In such a case it may be desirable to ignore the $D_{IR}$ values of 60 or more in memory 51 and stretch out the values of the $D_{IR}$'s with smaller values. This can be achieved by converting the numbers in the bytes in memory 51 in a linear or other functional relationship so that a value less than 60, e.g., 59 is converted into 63 and all other $D_{IR}$ values from 0 to 59 are also converted to larger numbers. On the other hand, if the total count in counters 0-3 of set 45 is very high it indicates no exposure. In such event contrast stretching may be achieved by decreasing the values of $D_{IR}$ in memory 51. For example, a $D_{IR}=4$ may be converted into a 0 and larger values decreased proportionately.

The contrast stretching may be achieved by known circuitry, which are represented in FIG. 2 by block 60. Basically once the stretching parameters or criteria are decided, based on the counts in the counters of set 54 and the distribution of the total count of 1000 in these counters each $D_{IR}$ byte may be read out of memory 51 to circuit 60 and after stretching, i.e., after increasing or decreasing it, it is restored as a stretched $D_{IR}$ in memory 51. If desired, the stretched $D_{IR}$ values may be stored in a memory, other than $D_{IR}$ memory 51.

A $D_R$ memory 52 and an associated set 55 of 64 histogram counters are provided to respond to the $D_R$ numbers from A/D converter 34. They function and operate in a manner analogous to that of memory 51 and set 54. Likewise, a $D_G$ memory 52 and an associated set 56 of 64 $D_G$ histogram counters are provided to respond to the $D_G$ numbers from A/D converters 33. In FIG. 2 a single contrast stretch circuit 60 is shown. Clearly with a single unit the numbers in memories 51-53 can only be stretched successively. However, if desired, three separate contrast stretch circuits, like circuit 60, may be provided, one for each memory, so that contrast stretching may be performed in parallel.

In practice, after all the pixels (e.g., 1000) are scanned one observes the count distribution in each of sets 54-56. If they all indicate no exposure or saturated exposure, instead of stretching the numbers in each of memories 51-53 a second scanning operation may be performed with a different exposure level, to produce 1000 new sets of $D_{IR}$, $D_R$, and $D_G$ numbers. However, if one or more of the histograms shows satisfactory distribution, contrast stretching is performed on the numbers in the other memories.

Once the numbers in one or more of memories 51-53 have been stretched the ratio numbers are produced.

This is achieved by successively reading out the numbers from the three memories 51-53 and dividing corresponding numbers, i.e., the $D_{IR}$, $D_R$ and $D_G$ numbers from the same pixel, in dividers 36-38 to provide the ratio numbers $D_{IR/R}$, $D_{R/G}$ and $D_{IR/G}$, as hereberefore described in connection with FIG. 1. The outputs of dividers 36-38, i.e., the ratio numbers $D_{IR/R}$, $D_{R/G}$, and $D_{IR/G}$ are stored in memories 61-63 respectively. Thus, at the end of this operation each of these memories stores 1000 numbers, each representing the ratio of the reflectance from a given pixel of light of different wavelengths.

After the ratio numbers are stored in memories 61-63 they are in condition to be fed to the color monitor 40. Basically, corresponding ratio numbers from the three memories 61-63 are read out simultaneously and fed as the three color-control inputs to the control monitor 40, to produce the visual color display and/or a hard color print. It should be pointed out that after contrast stretching, the reading out of the numbers of memories 51-53, the division performed by dividers 36-38, the entering of the three ratio numbers for each pixel into memories 61-63 and their reading out to monitor 40 can all be performed in parallel, thus greatly reducing data processing time. The entry of all data numbers to or from the various memories, as well as, the operation of the circuit 60 and the dividers 36-38 are all controllable by a control circuit 65, which is assumed to be connected to the various circuits and memories by control lines 65a-65n.

In the foregoing description it was assumed that the ratio numbers in memories 61-63 do not undergo stretching. If desired three sets of histogram counters, like 54-56 may be associated with memories 61-63 to stretch the ratio numbers in one or more of these memories, as hereberefore described in connection with the numbers in memories 51-53.

Heretofore it was assumed for explanatory purposes that each of the numbers in any of memories 51-53, i.e., $D_{IR}$, $D_R$ and $D_G$ assumes any of 64 values, that is, between 0 and 63 inclusive. As to the ratio numbers in memories 61-63 they too may be controlled not to exceed a value of 63. Thus, each of them may be stored in a 6-bit byte.

Figure 3:
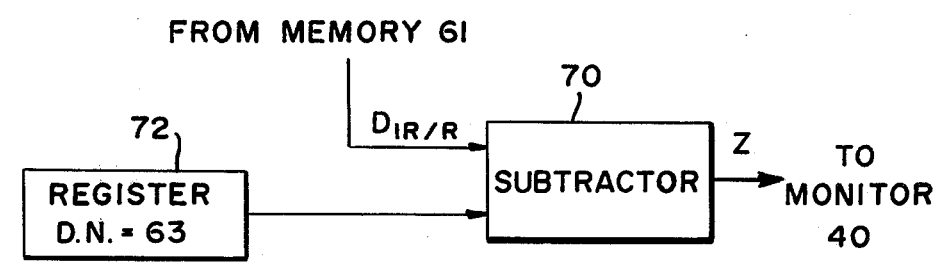
FIG. 3 is a simple block diagram of circuitry which may be incorporated in another embodiment of the invention.

In one particular embodiment, which was actually reduced to practice, it has been discovered that very satisfactory color prints and/or displays are produced for the analysis of burns if the ratio numbers $D_{IR/R}$ from memory 61 instead of being supplied directly to color monitor 40, as one of its inputs, are first inverted by making the small value numbers high, e.g., a $D_{IR/R}=0$ into $D_{IR/R}=1$ into $D_{IR/R}=62$, and large value numbers, e.g., $D_{IR/R}=63$ small, e.g., $D_{IR/R}=0$. This can be accomplished quite easily by subtracting each $D_{IR/R}$ number as it is read out from memory 61 from a value of 63 and sending the difference number as the input to monitor 40. In FIG. 3 a subtractor 70 is shown to which a digital number (D.N.) of a value 63 is applied as one input from a fixed register 72. The other input to subtractor 70 is the $D_{IR/R}$ number supplied from memory 61. The output of the subtractor 70 is the input to the monitor 40. It should be apparent that with such an arrangement the $D_{IR/R}$ input to the monitor is $Z=63-D_{IR/R}$, where $D_{IR/R}$ is the number supplied to subtractor 70 from memory 61.

From the foregoing it should be appreciated that the system and method of the present invention eliminate all the disadvantages of the burn diagnosis system, proposed in the prior art. Therein 3 separate color photographs are taken of the burned skin with 3 separate cameras. Even though the cameras may be placed close to one another, since the photographs are taken with different cameras the produced photographs have to be registered to insure the proper overlapping of corresponding pixels in them. Such registration is needed to be able to subtract optical densities in order to obtain a ratio of reflectance, since in film it is the logarithm of reflectance that is part of the function which affects optical density.

In the present invention, by the use of 3 photosensitive devices, e.g., linear silicon diode arrays 20, 25 and 30, three signals are produced simultaneously from each pixel, eliminating the need of taking and developing photographs which require subsequent registration. Also, these 3 signals have amplitudes which are related directly to the reflectance of light of different wavelengths from the particular pixel. Thus, ratio signals of reflectance are obtainable by merely dividing different pairs of these 3 signals. By converting the 3 signals into digital numbers, hereberefore designated $D_{IR}$, $D_R$ and $D_G$, these numbers can be stored in known digital computer memories for subsequent processing and use, as hereberefore described.

As described in connection with FIG. 1, with the system of the present invention, outputs, e.g., visual color display and/or hard color prints may be produced on a real time basis, i.e., at the time the skin is actually scanned. If, however, contrast stretching or other processing of the generated numbers $D_{IR}$, $D_R$, $D_G$, is desired to enhance the outputs, some delay in the outputs may result. However since modern digital data processing systems, e.g., computers, are capable of high speed operation, the storing of these numbers and their subsequent processing can be achieved with minimal delay. Thus, enhanced outputs for more accurate diagnosis can be achieved on a near-real time basis, in sufficient time for a physician to analyze the outputs and aid in the patient treatment.

Figure 4:
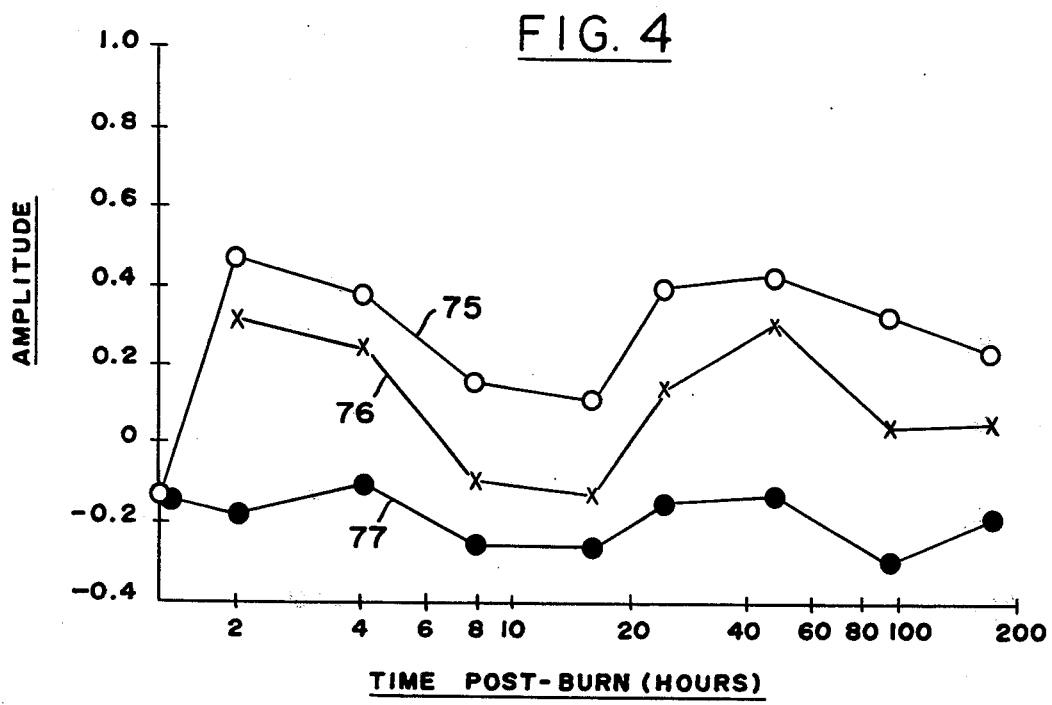
FIGS. 4 and 5 are plots of signal amplitudes versus post-burn time.
Figure 5:
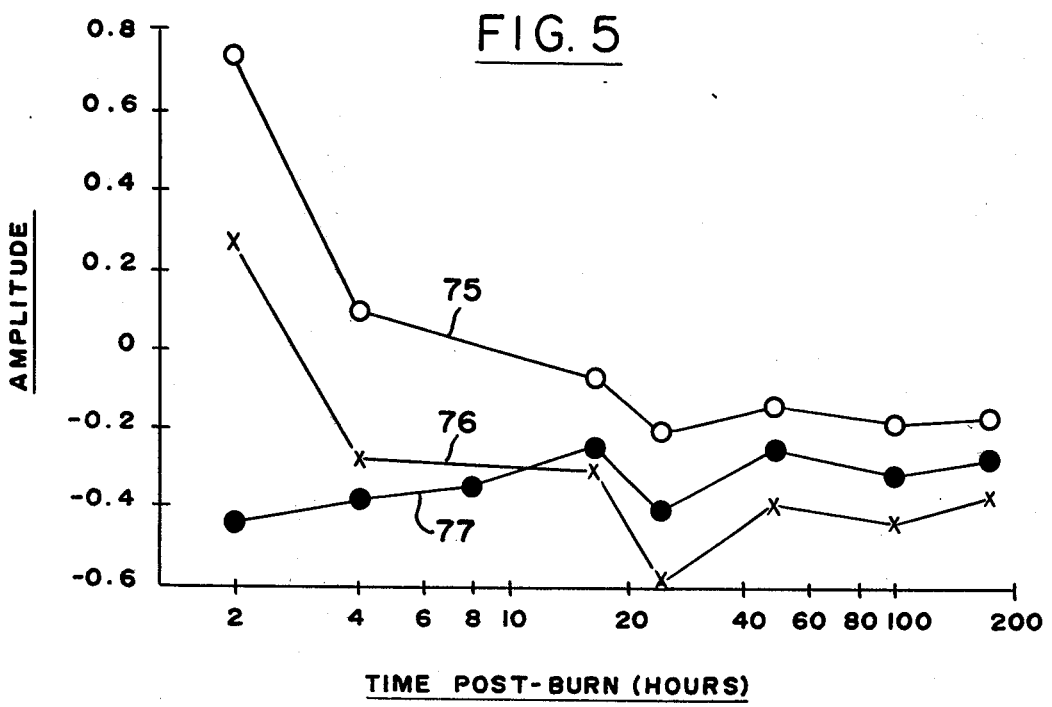

In addition to the foregoing description it should be appreciated that since the numbers $D_{IR/R}$, $D_{R/G}$ and $D_{IR/G}$ which are generated for each scanned pixel are present in memories 61-63, one can scan the skin during selected postburn points in time to observe changes in these numbers relative to one another, from which additional information on the depth of the burns may be determined. This aspect may best be explained in connection with FIGS. 4-6. FIG. 4 is a diagram of the values of $D_{IR/R}$ (represented by line 75 with the small circles), of the values of $D_{IR/G}$ (represented by line 76 with the x's) and of the values of $D_{R/G}$ (represented by line 76 with the small dots) as a function of post burn time in hours. FIG. 5 is a similar diagram. As seen from FIG. 4 therein $D_{IR/R} > D_{IR/G} > D_{R/G}$. This condition has been found to be present for a partial-thickness burn. On the other hand, in FIG. 5, it is seen that even though during the first few (about 10) hours after the burn $D_{IR/G} > D_{R/G}$, after about 16 hours $D_{R/G} > D_{IR/G}$. Such information seems to indicate full-thickness burn.

In FIGS. 4 and 5 the abcissa is time and the ordinate is amplitude. In plotting these graphs one can use as the amplitude for each ratio number, e.g., $D_{IR/R}$ the average of all the numbers in memory 61. Preferably, the numbers $D_{IR/R}$ for a particular pixel or several pixels at a particular area of interest may be used.

With the particular system of the present invention, this can be accomplished quite easily, efficiently, and with minimum complexity. For example, the skin 11 may be scanned repeatedly at desired hours after burn to produce a series of color displays and/or prints. In addition, one or more numbers related to a particular pixel or pixels for interest, stored in each of memories 61–63 may be averaged (if more than one pixel number is used) and fed to a plotter 80, as shown in FIG. 6 to produce the plots like those shown in FIGS. 4 and 5.

Although herebefore the invention has been described in the context of scanning burned skin to aid in its diagnosis, the invention is not intended to be limited thereto. Skin is but one example of surface tissue. Thus, the invention may be used to provide information of any surface tissue by employing the multispectral imaging technique herebefore described, i.e., by generating a plurality of signals which relate to the reflectance of light of different wavelengths from each incremental area of the surface tissue of interest. These signals may be processed to produce derived signals, one example to which are the ratio numbers, which can then be used to provide an output, e.g., the visual color display and/or the hard color copies, to aid in diagnosing the surface tissue condition or changes in its characteristics.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A system for generating data for use in diagnosing the condition of surface tissue of a patient, comprising:
    first means for scanning the surface tissue of a patient and for generating simultaneously n different signals from the light reflected from each incremental area of the surface tissue, each different signal being directly related to the reflectance of light of a different wavelength range from said incremental area, n being an integer not less than 2;
    second means for providing a preselected number of derived signals from the n signals, associated with each incremental area, each derived signal being a function of at least two of said n signals; and
    output means including at least means responsive to said derived signals for providing output data, indicative of the surface tissue condition.

2. The system as described in Claim 1 wherein n=3, said 3 signals representing the reflectance of infrared, red, and green light from each incremental area, said signals being definable as $D_{IR}$, $D_R$ and $D_G$, respectively.

3. The system as described in claim 2 wherein said second means provide three ratio signals definable as $D_{IR/R}$, $D_{IR/G}$ and $D_{R/G}$, where $D_{IR/R}=D_{IR}/D_R$, $D_{IR/G}=D_{IR}/D_G$ and $D_{R/G}=D_R/D_G$.

4. The system as described in claim 1 wherein said first means include at least first, second and third photosensitive devices, each providing an analog signal which is directly related to light received thereby and at least second and third filters, respectively positioned in the paths of light directed to said first, second and third photosensitive devices, for controlling the wavelengths of light receivable by said devices, and means for successively scanning incremental areas of the surface tissue and for simultaneously directing light to all three devices from each of said scanned incremental areas.

5. The system as described in claim 4 further including converting means, for converting the analog signals provided by each of said devices into digital numbers, and wherein said surface tissue is a patient's skin and said first, second and third filters are an infrared filter, a red filter and a green filter respectively, said converting means provide a digital number definable as $D_{IR}$ which is directly related to infrared light received to said first device, a digital number definable as $D_R$ which is directly related to red light received by said second device and a digital number definable as $D_G$ which is directly related to green light received by said third device.

6. The system as described in claim 5 wherein said second means include means for providing three separate derived signals which are digital ratio numbers, definable as $D_{IR/R}$, $D_{IR/G}$ and $D_{R/G}$, where $D_{IR/R}=D_{IR}/D_R$, $D_{IR/G}=D_{IR}/D_G$, and $D_{R/G}=D_R/D_G$, said output means providing said color presentation as a function of $D_{IR/R}$, $D_{IR/G}$ and $D_{R/G}$ of each incremental area.

7. The system as described in claim 6 further including means for providing an indication of the distribution of all the numerical values of each of the $D_{IR}$, $D_R$ and $D_G$ digital numbers generated in response to scanning a preselected number of incremental areas.

8. The system as described in claim 7 further including means for varying selected ones of any of said $D_{IR}$, $D_R$ and $D_G$ numerical values as a function of their numerical value distribution.

9. The system as described in claim 1 further including means for providing an indication of the distribution of all the values of each of said n signals which are generated by said first means in response to scanning a preselected number of incremental areas of said surface tissue.

10. The system as described in claim 9 further including means for varying the values of selected ones of corresponding signals of said n signals as a function of their value distribution.

11. Apparatus for diagnosing the condition of surface tissue of a patient, comprising:
    means for directing light at the tissue;
    a plurality of photosensitive detectors which each generate an output dependent on the intensity of light falling thereon;
    a beamsplitter for directing portions of the same light reflected from each of a multiplicity of pixels on the tissue surface, towards each of said detectors;
    a plurality of filter means, each disposed between said beamsplitter and a corresponding one of said detectors, to allow a different selected wavelength range to reach the corresponding detector;
    a circuit connected to said plurality of detectors for generating a derived signal corresponding to each of said pixels, wherein the signal is a function of the outputs of a plurality of said detectors resulting from the incidence of light thereon from the same pixels; and
    output means responsive to said circuit for providing output data indicative of the surface tissue condition.

12. A method of generating data useful in the diagnosis of the depth of burns of burned skin of a patient, the steps comprising:
    illuminating said burned skin;
    scanning incremental areas of said illuminated burned skin;

simultaneously sensing light at n different wavelength ranges reflected by each incremental area, and simultaneously generating n signals related thereto; from the n signals generated from the light reflected from each incremental area, generating a plurality of derived signals, each of said derived signals being a function of at least two of said n signals; and utilizing the derived signals related to each incremental area to produce output data indicative of the condition of the scanned skin.

13. A method as described in claim 12 wherein three signals are simultaneously generated for each incremental area which are directly related to infrared, red and green light respectively, reflected by the incremental area, the three signals being definable as $D_{IR}$, $D_R$ and $D_G$, and said step of generating derived signals includes generating signals which are each a function of at least two of said signals $D_{IR}$, $D_R$ and $D_G$.

14. A method as described in claim 13 wherein said step of generating derived signals includes generating signals of the values $D_{IR/R} = D_{IR}/D_R$, $D_{IR/G} = D_{IR}/D_G$ and $D_{R/G} = D_R/D_G$.

15. A method as described in claim 14 wherein said step of utilizing includes producing a color image wherein each incremental area of the image is of a color determined by the signals $D_{IR/R}$, $D_{IR/G}$ and $D_{R/G}$ at the same incremental skin area.

* * * * *